(12) United States Patent
Schleifer (10) Patent No.: US 9,165,751 B1
(45) Date of Patent: Oct. 20, 2015

(54) SAMPLE ATOMIZATION WITH REDUCED CLOGGING FOR ANALYTICAL INSTRUMENTS

(71) Applicant: Agilent Technologies, Inc., Santa Clara, CA (US)

(72) Inventor: Arthur Schleifer, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/298,753

(22) Filed: Jun. 6, 2014

(51) Int. Cl.
*H01J 49/04* (2006.01)
*H01J 49/10* (2006.01)
*H01J 49/26* (2006.01)
*G01J 3/443* (2006.01)
*G01N 1/28* (2006.01)
*B05B 7/04* (2006.01)

(52) U.S. Cl.
CPC ........... *H01J 49/0454* (2013.01); *B05B 7/0416* (2013.01); *G01J 3/443* (2013.01); *G01N 1/28* (2013.01); *H01J 49/10* (2013.01); *H01J 49/26* (2013.01)

(58) Field of Classification Search
USPC ......................................................... 250/288
See application file for complete search history.

(56) References Cited

U.S. PATENT DOCUMENTS

| | | | | |
|---|---|---|---|---|
| 5,233,156 | A | * | 8/1993 | Chan et al. ............... 219/121.52 |
| 6,166,379 | A | * | 12/2000 | Montaser et al. ............. 250/288 |
| 7,106,438 | B2 | | 9/2006 | Morrisroe et al. |
| 7,671,329 | B2 | | 3/2010 | Sakata et al. |
| 8,272,576 | B2 | | 9/2012 | Doak et al. |

OTHER PUBLICATIONS

DePonte et al., Gas Dynamic Virtual Nozzle for Generation of Microscopic Droplet 5 Streams, J. Phys. D: Appl. Phys. 41 195505 (2008).

* cited by examiner

*Primary Examiner* — Kiet T Nguyen (57) ABSTRACT

An aerosol is produced by flowing a liquid sample through a gas-assisted nebulizer. The liquid exits from an outlet into a coaxial flow of gas. The outlet includes a sharp edge that inhibits or prevents accumulation of precipitates from the liquid, thereby reducing or eliminating clogging, which is particularly useful for a samples containing high concentrations of dissolved particles. The aerosol may be introduced into a plasma such that molecules are broken into atoms. The atomization may be followed by an analysis such as by optical emission spectrometry or mass spectrometry.

20 Claims, 4 Drawing Sheets

SAMPLE ATOMIZATION WITH REDUCED CLOGGING FOR ANALYTICAL INSTRUMENTS

TECHNICAL FIELD

The present invention relates generally to atomization of sample material by nebulization and exposure to plasma, which may be done to electronically excite and/or ionize the sample material in preparation for analysis.

BACKGROUND

Certain analytical instruments require that a liquid sample be nebulized (vaporized), i.e., converted to an aerosol (a fine spray or mist), and then broken down to atoms in preparation for analysis. Thus, a nebulizer (typically pneumatically assisted) is often part of the sample introduction system of an optical emission spectrometer (OES, also termed an atomic emission spectrometer or AES) or a mass spectrometer (MS). The aerosol from the nebulizer is directed into a plasma plume generated by a plasma source, which is often configured as a flow-through torch. The plasma is typically inductively coupled plasma (ICP) or microwave induced plasma (MIP). Exposure to plasma breaks the sample molecules down to atoms.

In the plasma, the sample atoms repeatedly lose electrons (are ionized) and recombine with electrons. During this process, the atoms emit electromagnetic radiation (light) at wavelengths characteristic of their elemental identities. In an OES, this light is collected and focused by optics and directed to an analyzer, which may include, for example, a diffraction grating. The analyzer spectrally resolves the light into its component wavelengths, enabling the intensity of the light at each wavelength (respective abundances of the wavelengths) to be measured by an optical detector. The OES system then presents the data so acquired as a spectrum of atomic emission lines. The intensity of each line is indicative of the concentration (abundance) of the corresponding element of the sample.

In an MS, ions of the sample atoms are extracted from the plasma source and directed as an ion beam into a mass analyzer. The mass analyzer applies a time-varying electrical field, or a combination of electrical and magnetic fields, to spectrally resolve different types of ions on the basis of their mass-to-charge (m/z) ratios, enabling an ion detector to count each type of ion of a given m/z ratio. The MS system then presents the data so acquired as a spectrum of mass (m/z ratio) peaks (respective abundances of the m/z ratios). The intensity of each peak is indicative of the concentration (abundance) of the corresponding element of the sample.

Generally, the structures and operations of various types of analytical nebulizers, plasma sources, OES instruments, and MS instruments are known to persons skilled in the art, and accordingly are only briefly described herein as necessary for understanding the subject matter being disclosed.

In addition to the analytes (the sample atoms or ions for which data is sought), the liquid sample may contain a high concentration of dissolved salts (e.g., metal salts, such as in a sample of seawater) or total dissolved solids (TDS). During the process of converting the liquid sample to liquid drops in a gas-assisted nebulizer, the salt or dissolved solids may precipitate out of the solution and accumulate at any orifice of the nebulizer through which the sample material flows, such as the exit of the nebulizer. Over time, more precipitates form and eventually clog the exit or other orifice and the nebulizer stops working, consequently disrupting the operation of the associated analytical system. Upon detecting the clog, the operator of the system must shut the system down and remove the nebulizer for cleaning.

As an example, a gas-assisted nebulizer often has a concentric configuration in which the bulk liquid sample flows through a central tube (or capillary) and the nebulizing gas (e.g., argon, nitrogen, etc.) flows through an outer tube surrounding the central tube. A meniscus is formed at the outlet of the central tube from which the bulk liquid sample exits. When the meniscus becomes large enough, the surface of the meniscus is exposed to the gas flowing by the outlet of the central tube. A liquid drop is pulled from the meniscus when the force of the gas is strong enough and the surface of the meniscus large enough to overcome the surface tension of the liquid. Conventional nebulizers such as this type have features that present locations where the liquid is stagnant and not exposed to the gas flowing by the central tube outlet. Over time, the concentration of the salt or dissolved solid in the liquid can increase to the point where the salt or dissolved solids will precipitate out of solution. One this process begins, the precipitate formation increases and eventually a clog will occur.

One way to minimize clogging is to dilute the liquid sample and thereby lower the salt or solid concentration as described, for example, in U.S. Pat. No. 7,671,329, the content of which is incorporated by reference herein in its entirety. However, dilution may lower the measurement signals acquired and reduce the sensitivity of the spectrometer or other analytical instrument.

Therefore, there is a need for an analytical nebulizer, sample atomizer, and associated system in which clogging is minimized in a manner that does not require dilution of a liquid sample.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for producing an aerosol from a liquid sample includes: providing a nebulizer including a first nebulizer tube terminating at a first nebulizer outlet, and a second nebulizer tube coaxially surrounding the first nebulizer tube and terminating at a second nebulizer outlet; flowing a carrier gas through the second nebulizer tube; flowing the liquid sample through the first nebulizer tube such that the liquid sample becomes entrained in the carrier gas and is broken into droplets to form the aerosol; and flowing the aerosol out from the second nebulizer outlet, wherein the first nebulizer outlet includes a sharp edge at which an inside diameter of the first nebulizer tube is substantially the same as an outside diameter of the first nebulizer tube, such that the sharp edge prevents accumulation of precipitates from the liquid sample at the first nebulizer outlet.

According to another embodiment, the liquid sample comprises a high concentration of dissolved salt or dissolved solid material wherein the sharp edge prevents accumulation of precipitates of salt or solid material at the first nebulizer outlet.

According to another embodiment, a method for atomizing a liquid sample includes: producing an aerosol according to any of the methods disclosed herein; generating plasma; and injecting the aerosol into the plasma.

According to another embodiment, a method for atomizing a liquid sample includes: nebulizing the liquid sample to produce an aerosol, by flowing a carrier gas through a nebulizer, and flowing the liquid sample through the nebulizer such that the liquid sample becomes entrained in the carrier gas and is broken into droplets to form the aerosol, wherein: the nebulizer comprises a first nebulizer tube terminating at a first nebulizer outlet, and a second nebulizer tube coaxially surrounding the first nebulizer tube and terminating at a second nebulizer outlet; the liquid sample is flowed through the first nebulizer tube, the carrier gas is flowed through the second nebulizer tube, and the aerosol is emitted from the second nebulizer outlet; and the first nebulizer outlet comprises a sharp edge at which an inside diameter of the first nebulizer tube is substantially the same as an outside diameter of the first nebulizer tube, such that the sharp edge prevents accumulation of precipitates from the liquid sample at the first nebulizer outlet; and further including: generating a plasma; and injecting the aerosol into the plasma.

In some embodiments, generating plasma comprises generating inductively coupled plasma or microwave induced plasma.

According to another embodiment, a method for analyzing a liquid sample includes: atomizing the liquid sample according to any of the methods disclosed herein to produce sample atoms; and measuring an attribute of the sample atoms.

According to another embodiment, a sample atomizer includes: a nebulizer including: a first nebulizer tube defining a first fluid path, and including an inside diameter, an outside diameter, and a first nebulizer outlet, the first nebulizer outlet comprising a sharp edge at which the inside diameter is substantially the same as the outside diameter; and a second nebulizer tube coaxially surrounding the first nebulizer tube and defining a second fluid path of annular cross-section, the second nebulizer tube including a second nebulizer outlet positioned such that the first fluid path merges into the second fluid path. The sample atomizer further includes: a plasma source including a sample inlet communicating with the second nebulizer outlet, a plasma-forming gas inlet, and an energy source configured for generating plasma in the plasma source.

In some embodiments, the nebulizer may be configured as a gas dynamic virtual nozzle.

According to another embodiment, a sample analysis system includes: a sample atomizer of according to any of the embodiments disclosed herein; and an analytical instrument configured to acquire data from sample atoms produced by the sample atomizer.

In some embodiments, the analytical instrument is or includes a spectrometer such as, for example, a mass spectrometer or an optical emission spectrometer.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

In the context of the present disclosure, for convenience the term "liquid" encompasses a solution and also a suspension in which solid particles are present in the liquid.

In the context of the present disclosure, the term "atomization" refers to the process of breaking molecules down to atoms. "Atomizing" a liquid sample entails nebulizing the liquid sample to form an aerosol, followed by exposing the aerosol to plasma.

In the context of the present disclosure, a "liquid sample" includes one or more different types of analytes of interest (e.g., metals) dissolved or otherwise carried in a liquid matrix. The liquid matrix may be or include water and/or other solvents, soluble materials such as salts and/or total dissolved solids (TDS), and may further include other compounds that are not of analytical interest.

In certain embodiments disclosed herein, the liquid sample may include a high concentration of dissolved salts and/or TDS. Generally, a "high" concentration means that the concentration of dissolved salts and/or TDS is high enough to cause clogging of an analytical nebulizer, particularly a nebulizer operating as part of an optical emission spectrometer (OES) or a mass spectrometer (MS) system, during normal operation. One example of high concentration, but not limiting to the broad aspects of the subject matter disclosed herein, is a concentration of dissolved salts and/or TDS of 1000 ppm or greater. Another example of high concentration is 10,000 ppm or greater. Another example of high concentration is 5000 ppm or greater. In another example, sea water has a salt concentration of about 35,000 to 40,000 ppm (about 3.5 to 4%).

Figure 1:
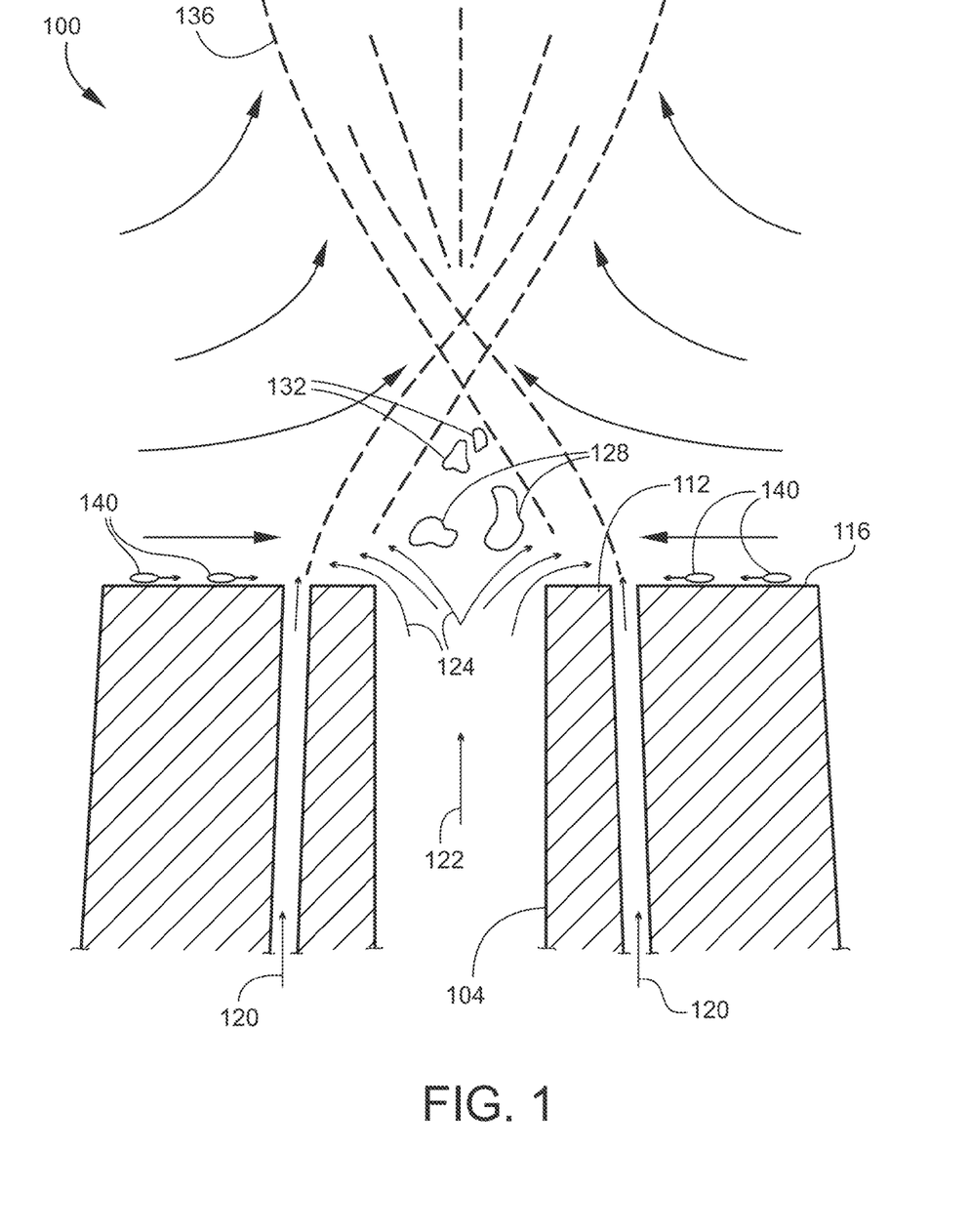
FIG. 1 is a schematic cross-sectional view of the distal (tip) section of an example of conventional nebulizer having a known concentric configuration.

FIG. 1 is a schematic cross-sectional view of the distal (tip) section of an example of conventional nebulizer 100 having a known concentric configuration. The nebulizer 100 includes a central tube 104 for conducting a flow of liquid sample along a longitudinal (typically central) axis of the nebulizer 100, and an outer tube 108 coaxially surrounding the central tube 104, thereby forming an annular conduit for conducting a flow of nebulizing gas (or carrier gas). The central tube 104 terminates at a distal edge (or end surface) 112 that defines the liquid outlet of the central tube 104. The outer tube 108 likewise terminates at a distal edge (or end surface) 116 that with the distal edge 112 defines the annular gas outlet of the annular gas conduit. The central tube 104 and outer tube 108 are typically flush, i.e., occupy the same axial position as illustrated. Conventionally, both distal edges 112 and 116 are flat (orthogonal to the longitudinal axis) as illustrated. Generally, flat features are easier to manufacture as compared to other geometrical features such as sharp edges, and are more robust and thus less prone to damage.

In operation, a flow of nebulizing gas is established through the annular gas conduit as illustrated by arrows 120. A flow of liquid sample is then established through the central tube 104 as illustrated by an arrow 122. The liquid sample exits the liquid outlet of the central tube 104 and begins to diverge, as illustrated by liquid streamlines 124. The gas exiting the gas outlet of the annular gas conduit coaxially envelops the liquid sample. Liquid pulled by the gas flow fragments into coarse droplets 128, which in turn further fragment into fine droplets 132. This process results in the formation of an aerosol or spray plume 136 comprising fine droplets 132 entrained in the gas. As illustrated, some droplets 140 may settle on or adhere to the flat distal edges 112 and 116 of the central tube 104 and outer tube 108. The flat distal edges 112 and 116 are areas where the droplets 140 stagnate. Such droplets 140 may or may not eventually become entrained or re-entrained into the gas flow, but in all cases the areas of stagnation presented by the flat distal edges 112 and 116 cause the formation of, or at least the accumulation of, precipitates (e.g., salts and/or solids) on these surfaces, which in turn leads to clogging of the liquid outlet and/or gas outlet as described above.

Figure 2:
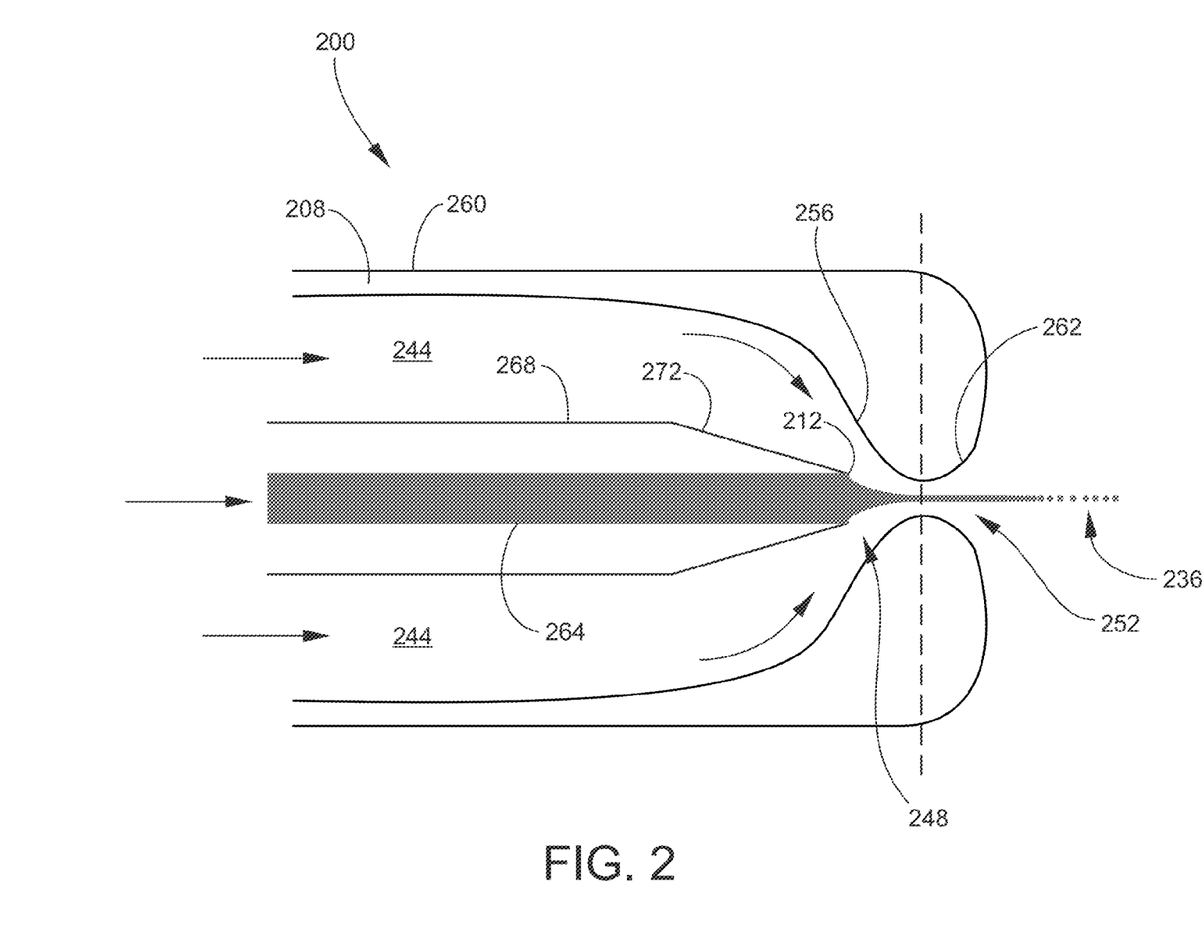
FIG. 2 is a schematic cross-sectional view of the distal (tip) section of an example of a nebulizer according to some embodiments of the present disclosure.

FIG. 2 is a schematic cross-sectional view of the distal (tip) section of an example of a nebulizer 200 according to some embodiments of the present disclosure. The nebulizer 200 includes a central, first nebulizer tube 204 defining a first fluid path (liquid path in the present example) for conducting a flow of liquid sample along a longitudinal (typically central) axis of the nebulizer 200. The nebulizer 200 also includes an outer, second nebulizer tube 208 coaxially surrounding the first nebulizer tube 204, thereby forming an annular conduit 244 defining a second fluid path (gas path in the present example) for conducting a flow of nebulizing gas (or "carrier gas"). The first nebulizer tube 204 terminates at a distal edge 212 that defines a first nebulizer outlet (liquid outlet) 248 of the first nebulizer tube 204. The second nebulizer tube 208 terminates at a second nebulizer outlet (or nebulizer exit) 252. As illustrated, the first nebulizer tube 204 and the second nebulizer tube 208 may be radially symmetric relative to the longitudinal axis. No specification limitation is placed on the materials utilized for fabricating the first nebulizer tube 204 and the second nebulizer tube 208. Examples include, but are not limited to, fused silica and various glasses, polymers, and metals.

The inside diameter of the second nebulizer outlet 252 is typically greater than, or at least the same or substantially the same as, the inside diameter of the first nebulizer outlet 248 to help prevent clogging due to particles in the liquid stream. In other embodiments, inside diameter of the second nebulizer outlet 252 may be less than the inside diameter of the first nebulizer outlet 248. Generally, the inside diameters of the first nebulizer outlet 248 and the second nebulizer outlet 252, as well as the liquid flow rate and pressure in the first nebulizer tube 204 and the gas flow rate and pressure in the annular conduit 244, are specified as needed for generating an aerosol with a desired size or size distribution of the droplets. In some embodiments, the inside diameter of the first nebulizer outlet 248 is in a range from 20 to 100 µm. In some embodiments, the inside diameter of the second nebulizer outlet 252 is in a range from 50 to 100 µm.

The second nebulizer tube 208 is configured (i.e., the second nebulizer outlet 252 is positioned) such that the liquid flow path merges into the gas path, whereby the second nebulizer outlet 252 serves as the sole fluid exit from the nebulizer 200. For example, in the illustrated embodiment, this is achieved by configuring the second nebulizer tube 208 such that the second nebulizer outlet 252 is positioned downstream from the first nebulizer outlet 248, and the first nebulizer outlet 248 is positioned in the distal interior section of the second nebulizer tube 208. In the illustrated embodiment, the downstream position of the second nebulizer outlet 252 is achieved by forming the second nebulizer tube 208 to include a converging section 256 at its distal end that transitions down to the second nebulizer outlet 252. That is, the converging section 256 is characterized by the inside diameter (inside surface) of a main portion 260 of the second nebulizer tube 208 tapering (reducing) down to the inside diameter of the second nebulizer outlet 252. By this configuration, the annular cross-sectional flow area of the gas path transitions to a focused flow area in the space between the first nebulizer outlet 248 and the second nebulizer outlet 252, and the liquid flow path is directed into this flow area. By this configuration, the inside diameter of the second nebulizer outlet 252 has a minimum value at the termination of the converging section 256, which is delineated in FIG. 2 by a vertical dashed line.

In some embodiments, as illustrated, the converging section 256 may transition to a diverging section 262—that is, the second nebulizer outlet 252 may be defined by a converging-diverging section. As illustrated, the geometry or profile of the converging section 256 (or the converging section 256 and diverging section 262) may be smooth and rounded and the tapering (change in diameter) relatively gradual. In this case, the converging section 256 (or the converging section 256 and diverging section 262) is free of any sharp edges or abrupt changes in geometry.

In some embodiments, as illustrated, the flow area between the first nebulizer outlet 248 and the second nebulizer outlet 252 is focused along the longitudinal axis of the nebulizer 200, with both the first nebulizer outlet 248 and the second nebulizer outlet 252 being coaxial with the longitudinal axis and the second nebulizer outlet 252 being spaced at a downstream axial distance from the first nebulizer outlet 248. In other embodiments, the axis along which the second nebulizer outlet 252 is oriented may be offset from or at an angle to the axis along which the first nebulizer outlet 248 is oriented.

The first nebulizer tube 204 includes an inside surface 264 defining its inside diameter and an outside surface 268 defining its outside diameter. The inside diameter of the first nebulizer tube 204 may be constant (straight-walled) up to the distal edge 212 such that it also defines the inside diameter of the first nebulizer outlet 248. According to the present disclosure, the distal edge 212 is a sharp edge (in other words, the first nebulizer outlet 248 includes or is defined by a sharp edge). The sharp edge may be characterized as not presenting a flat end face, or as not presenting an appreciable surface area. The sharp edge may also be characterized as an edge at which the inside diameter of the first nebulizer tube 204 is substantially the same as the outside diameter of the first nebulizer tube 204. As may be seen by comparing FIG. 2 with FIG. 1, the configuration of the nebulizer 200 eliminates areas (such as the flat distal edges 112 and 116 shown in FIG. 1) where liquid tends to stagnate, evaporate, and consequently cause accumulation of solid material and eventual clogging. The sharp distal edge 212 may be formed by any suitable technique, depending on factors such as the size and composition of the first nebulizer tube 204. Examples include, but are not limited to, grinding and fast ion bombardment (FIB). As illustrated, the sharp distal edge 212 may be formed by beveling or tapering down the distal section of the outside surface 268. That is, the outside surface 268 has a beveled or tapered section 272 along which the outside diameter of the main section of the first nebulizer tube 204 tapers down to the outside diameter of the sharp distal edge 212—that is, the outside diameter of the first nebulizer tube 204 reduces down to the sharp distal edge 212. The tapered section 272 may include one bevel or taper angle. Alternatively, the tapered section 272 may include two or more different taper angles, such as smaller-angle bevel that transitions to a greater-angle bevel leading to the sharp distal edge 212. Such a dual- or multiple-bevel configuration may increase the robustness of the first nebulizer outlet 248 by leaving more material near the sharp distal edge 212.

In operation, a nebulizing (or carrier) gas is flowed through the annular conduit 244 at an appropriate flow rate and pressure, and converges toward the space just downstream from the first nebulizer outlet 248 (between the first nebulizer outlet 248 and the second nebulizer outlet 252). A liquid sample is flowed through the first nebulizer tube 204 at an appropriate flow rate and pressure, and exits the first nebulizer outlet 248 as a liquid stream or jet that is coaxially enveloped or sheathed by the gas stream. The liquid is then converted to an aerosol 236 as described above. The flow of the liquid and the gas may be laminar. In the embodiment specifically illustrated in FIG. 2, the forces exerted by the converging coaxial gas stream may compress the liquid stream (i.e., the liquid stream "necks down") to a narrower stream, the diameter of which may be smaller than the (minimum) inside diameter of the second nebulizer outlet 252. This type of geometry may be referred to as a gas dynamic virtual nozzle (GDVN). See, e.g., DePonte et al., Gas Dynamic Virtual Nozzle for Generation of Microscopic Droplet Streams, *J. Phys. D: Appl. Phys*. 41 195505 (2008). Depending on operating conditions, the fine droplets may be formed upstream of the second nebulizer outlet 252, and/or in the second nebulizer outlet 252, and/or downstream of the second nebulizer outlet 252 (as illustrated). The aerosol 236 may begin to diverge as a spray just after emerging from the second nebulizer outlet 252, or may at least initially emerge as a "single-file" train of droplets (as illustrated).

As noted above, the sharp distal edge 212 eliminates a major area of liquid stagnation, thereby greatly reducing or even eliminating clogging of either the first nebulizer outlet 248 or the second nebulizer outlet 252. Therefore, the nebulizer 200 is highly suitable for the processing of liquid samples containing high concentrations of dissolved salts and/or TDS.

Figure 3:
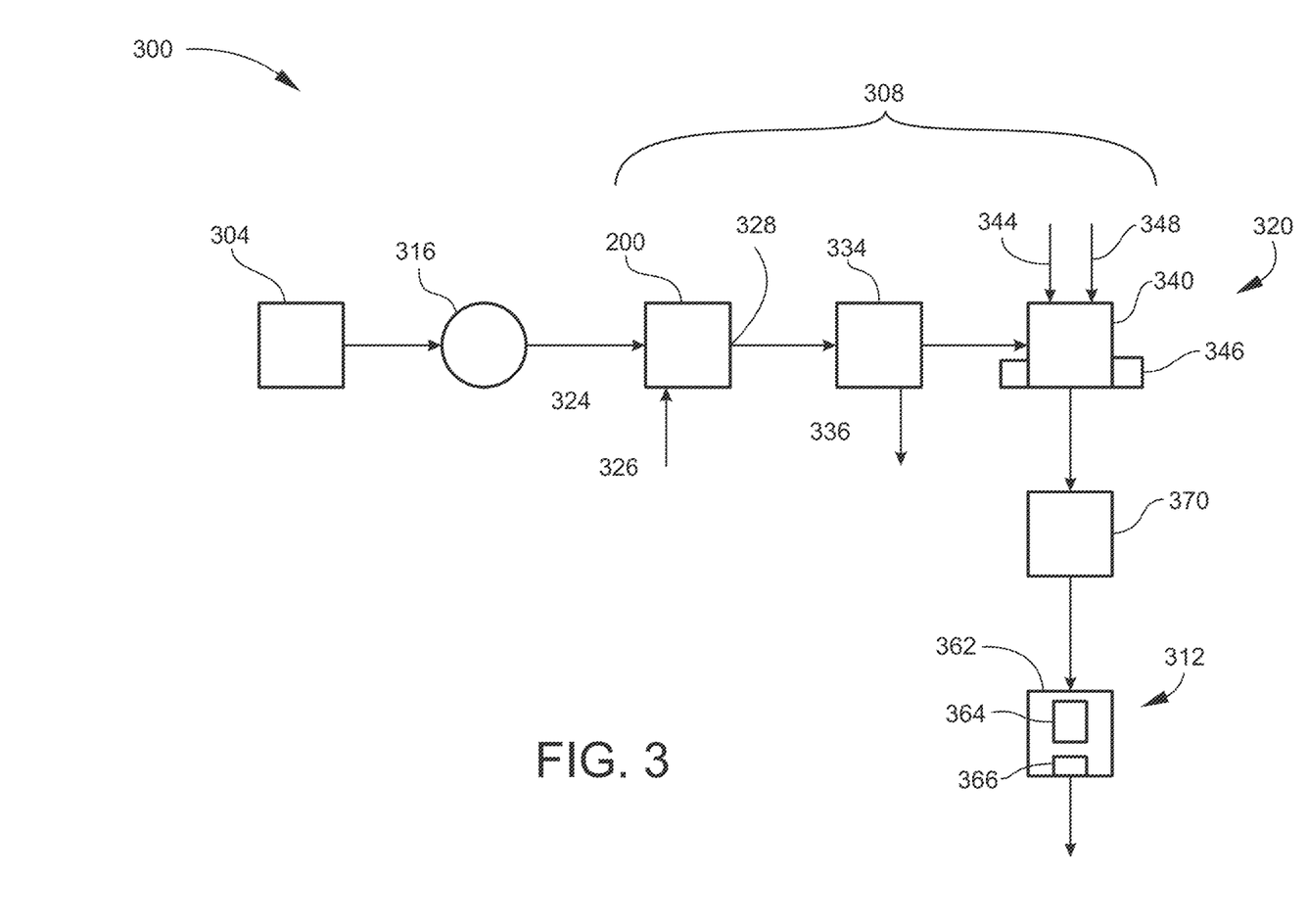
FIG. 3 is a schematic view of an example of a sample analysis system according to some embodiments.

FIG. 3 is a schematic view of an example of a sample analysis system 300 according to some embodiments. The sample analysis system 300 generally includes a liquid sample source 304, a plasma-based sample atomizer 308, and an analytical instrument 312. Generally, the sample atomizer 308 receives a flow of liquid sample from the sample source 304, converts the liquid sample into an aerosol, and flows the aerosol into a plasma to break sample molecules into atoms. The analytical instrument 312 then acquires measurement data from the atoms which, depending on its operating principle, may entail interacting with the sample atoms, with energy emitted from the sample atoms, or with ions derived from the sample atoms.

The sample source 304 may be any device or system for supplying a sample to be analyzed to the sample atomizer 308. A suitable pump (e.g., peristaltic pump, syringe, etc.) may be utilized to establish a flow of liquid sample into the sample atomizer 308. Alternatively, the sample source 304 may be or include a pressurized reservoir containing the liquid sample. In some embodiments, the source may be the output of a liquid chromatography (LC) instrument.

The sample atomizer 308 includes a nebulizer 200 configured according to embodiments described herein, and a plasma source 320. The nebulizer 200 includes a liquid sample inlet 324 communicating with the fluid line from the sample source 304 or from any pump 316 provided between the sample source 304 and the nebulizer 200. The liquid sample inlet 324 may be part of or otherwise communicate with the first nebulizer tube 204 (FIG. 2). The nebulizer 200 also includes a gas inlet 326 communicating with a carrier gas source, which may be part of or otherwise communicate with the second nebulizer tube 208 (FIG. 2). The carrier gas (or nebulizing gas) may be any inert gas suitable for nebulizing the liquid sample and compatible with the operation of the plasma source 320. Examples include, but are not limited to, argon and nitrogen. The nebulizer 200 also includes a nebulizer outlet (exit) 328, which may correspond to the second nebulizer outlet 252 (FIG. 2) described above.

The nebulizer 200 may communicate directly with the plasma source 320 via a fluid line and fittings. Alternatively, the sample atomizer 308 may include a spray chamber 334 fluidly intercoupled between the nebulizer 200 and the plasma source 320. As appreciated by persons skilled in the art, the spray chamber 334 is configured for removing larger (coarse) droplets from the aerosol whereby only fine droplets are introduced into the plasma source 320. For this purpose, the spray chamber 334 may include a housing enclosing a chamber interior. The spray chamber 334 may further include one or more internal structures (e.g., baffle, cylinder, etc.), which may be positioned such that the in-flowing larger droplets due to their greater momentum impinge on the internal structures while the smaller droplets avoid the internal structures. Larger droplets tend to adhere to the internal surfaces (e.g., inside surface of the housing, internal structures) of the spray chamber 334 and may be removed via a drain 336, while fine droplets remain entrained in the gas flow and are transmitted to the plasma source 320. No specific limitation is placed on the size range of "fine" droplets. As one non-limiting example, the size (diameter) of "fine" droplets may be on the order of micrometers (μm).

The sample aerosol may be emitted from the nebulizer 200 into an environment that is at or above atmospheric pressure. Such an environment may be, for example, a conduit leading directly into the plasma source 320, a conduit leading into the spray chamber 334 (if provided), or the spray chamber 334. In the present context, "at" atmospheric pressure encompasses "at or around" atmospheric pressure, i.e., the term "atmospheric pressure" is not limited to the standard atmospheric pressure of 760 Torr. As one non-limiting example, a pressure that is at (or around) atmospheric pressure may be on the order of hundreds of Torr. Also in the present context, "above" atmospheric pressure encompasses pressures greater than 760 Torr.

The plasma source 320 generally may have any configuration suitable for generating plasma, receiving a flow of sample aerosol from the nebulizer 200 (or the intervening spray chamber 334, if provided), and injecting the aerosol into the as-generated plasma, whereby the sample molecules of the aerosol are excited by the energized species of the plasma (electrons, plasma ions, etc.) and fragmented into atoms. The plasma source 320 generally may include a housing 340 enclosing a plasma source interior, a sample inlet 342 for conducting the aerosol into the interior, a plasma-forming gas inlet 344 for conducting a plasma-forming gas into the interior from a plasma-forming gas source, and an energy source 346 for generating plasma in the interior. In some embodiments the plasma source 320 may have a concentric tube configuration, which may be referred to as a plasma torch. For example, the aerosol may flow through a central tube and the plasma-forming gas may flow through an annular conduit formed between the central tube and a coaxially surrounding outer tube. The central tube and annular conduit may lead into a sample-plasma interaction region in proximity to components of the energy source 346 that generate the plasma in the interaction region (e.g., inductive coil, magnets, electrodes, etc.). Thus, by such configuration the central tube emits aerosol directly into the plasma plume. Optionally, the plasma source 320 may include an auxiliary gas inlet 348 from which an auxiliary gas is conducted along a flow path concentrically between the central aerosol flow path and the outer plasma-forming gas flow path, as described further below in conjunction with FIG. 4.

The plasma may be generated and sustained by various known techniques. As examples, the energy source 344 may include electrodes coupled to a direct current (DC), alternating current (AC) or radio frequency (RF) voltage source, and may further include one or more dielectric barriers, resonant cavities, microstrips, and/or magnets. Accordingly the plasma may be, for example, a DC or AC glow discharge, corona discharge, RF capacitive or inductive discharge, dielectric barrier discharge (DBD), or microwave discharge. In typical embodiments, the energy source 344 generates inductively coupled plasma (ICP) or microwave induced plasma (MIP). In the case of ICP, the energy source 344 may include an RF power source coupled to a work coil surrounding the interaction region of the plasma source interior. The work coil applies RF energy (e.g., 10 to 100 MHz) to the plasma-forming gas. In the case of MIP, the energy source 344 may include a power source coupled to an appropriate assembly of electrodes, magnets and resonant structures (e.g., a magnetron) to apply microwave energy (e.g., several GHz) to the plasma-forming gas. The plasma-forming gas may be a single gas species or a combination or two or more different species. In typical embodiments, the plasma-forming gas is argon or nitrogen. More generally, examples of plasma-forming gases include, but are not limited to, a noble gas (helium, neon, argon, krypton, or xenon), a combination of two or more noble gases, or a combination of a non-noble gas (e.g., hydrogen, or a halogen such as fluorine, chlorine or bromine) with one or more noble gases. Various types of plasmas, and the design and operating principles of various types of energy sources utilized to generate plasmas, are generally known to persons skilled in the art and thus for purposes of the present disclosure need not be described further. The nebulizing (carrier) gas and auxiliary gas may be the same as or different from the plasma-forming gas.

No specific limitation is placed on the size of either the nebulizer 200 or the plasma source 320. The size generally depends on the application and the sample flow rates contemplated. In some embodiments, the sample flow rates may be relatively low, such as on the order of 10 to 50 µL/min. In such a case, the nebulizer 200 and the plasma source 320 may be relatively small, i.e., may be configured as a "micro-nebulizer" and a "micro-plasma" source. For example, the plasma source 320 may be configured as a chip, which may be fabricated by known micro-fabrication techniques using suitable materials in a manner analogous to a microfluidic chip.

Generally, the analytical instrument 312 may be any instrument suitable for acquiring data from the sample atoms produced by the plasma source 320, such as for identifying the sample atoms, measuring the concentration (or abundance) of the sample atoms in the sample, etc. The analytical instrument 312 may be configured to measure (or detect) an attribute of the sample atoms. In some embodiments, the analytical instrument 312 may be a spectrometer that measures a spectral attribute. In a typical embodiment, the spectrometer includes housing 362 enclosing an analyzer 364 and a detector 366. Depending on the type of analytical instrument 312 provided, the sample analysis system 300 may include an interface 370 between the plasma source 320 and the analytical instrument 312, examples of which are described below.

In some embodiments, the analytical instrument 312 may be an optical emission spectrometer (OES, also termed an atomic emission spectrometer or AES). As appreciated by persons skilled in the art, an OES is configured for receiving photons emitted from the sample atoms as they relax from their excited states (induced by the plasma), spectrally resolving the photons on the basis of their respective wavelengths, and measuring the light intensity (abundance) at each wavelength. In the case of OES, the interface 370 may be optics (e.g., lenses) for collecting the light generated in the plasma source 320 and transmitting the light as a focused beam to the analyzer 364. The analyzer 364 may be, for example, a diffraction grating or other device configured for spectrally resolving the different wavelengths of the ensemble of photons comprising the light beam. The detector 366 may be any suitable optical detector such as, for example, one or more photomultiplier tubes (PMTs), photodiodes, charge coupled devices (CCDs), etc.

In other embodiments, the analytical instrument 312 may be a mass spectrometer (MS). As appreciated by persons skilled in the art, an MS is configured for receiving sample ions (sample atoms ionized by the plasma), spectrally resolving the sample ions on the basis of their respective mass-to-charge (m/z) ratios, and measuring the ion abundance (counting the ions) of each m/z ratio detected. In the case of MS, the interface 370 may be ion optics (e.g., lenses, multipole electrode sets, etc.) configured for extracting the sample ions from the plasma source 320 and transmitting them as a focused beam to the analyzer 364. The interface 370 may also represent one or more conical plates (e.g., sampling cone, skimmer cone, etc.) preceding the ion optics. As appreciated by persons skilled in the art, the conical plates have small central apertures through which the ion beam is directed, and serve as a gas conductance barrier between the plasma source 320 and the vacuum stages of the MS. The ion optics may be enclosed in one or more pump-down stages configured for lowering the pressure down to the very low vacuum level of the analyzer 364. The analyzer 364 is a mass analyzer. The structure and operation of various types of mass analyzers are known to persons skilled in the art. Examples of mass analyzers include, but are not limited to, multipole electrode structures (e.g., quadrupole mass filters, linear ion traps, three-dimensional Paul traps, etc.), time-of-flight (TOF) analyzers, electrostatic traps (e.g. Kingdon, Knight and ORBITRAP® traps) and ion cyclotron resonance (ICR) traps (FT-ICR or FTMS, also known as Penning traps). The detector 366 may be any device configured for collecting and measuring the flux (or current) of mass-discriminated ions outputted from the analyzer 364. Examples of ion detectors 366 include, but are not limited to, image current detectors, electron multipliers, photomultipliers, Faraday cups, and micro-channel plate (MCP) detectors.

The sample analysis system 300 may further include a system controller (not shown). The system controller may include one or more modules configured for controlling, monitoring and/or timing various functional aspects of the sample analysis system 300 such as, for example, controlling the operations of the sample source 304, the sample atomizer 308, and the analytical instrument 312, as well as controlling various gas flow rates, temperature and pressure conditions, and any other sample processing components provided between the illustrated devices. The system controller may also be configured for receiving the detection signals from the detector 366 and performing other tasks relating to data acquisition and signal analysis as necessary to generate data (e.g., an atomic emission line spectrum, a mass spectrum, etc.) characterizing the sample under analysis. The system controller may include a computer-readable medium that includes instructions for performing any of the methods disclosed herein. The system controller may include one or more types of hardware, firmware and/or software, as well as one or more memories and databases, as needed for operating the various components of the sample analysis system 300. The system controller typically includes a main electronic processor providing overall control, and may include one or more electronic processors configured for dedicated control operations or specific signal processing tasks. The system controller may also include one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller may include an operating system (e.g., Microsoft Windows® software) for controlling and managing various functions of the system controller.

It will be understood that FIG. 3 is a high-level schematic depiction of the sample analysis system 300 disclosed herein. As appreciated by persons skilled in the art, other components such as additional structures, devices, and electronics may be included as needed for practical implementations, depending on how the sample analysis system 300 is configured for a given application.

Figure 4:
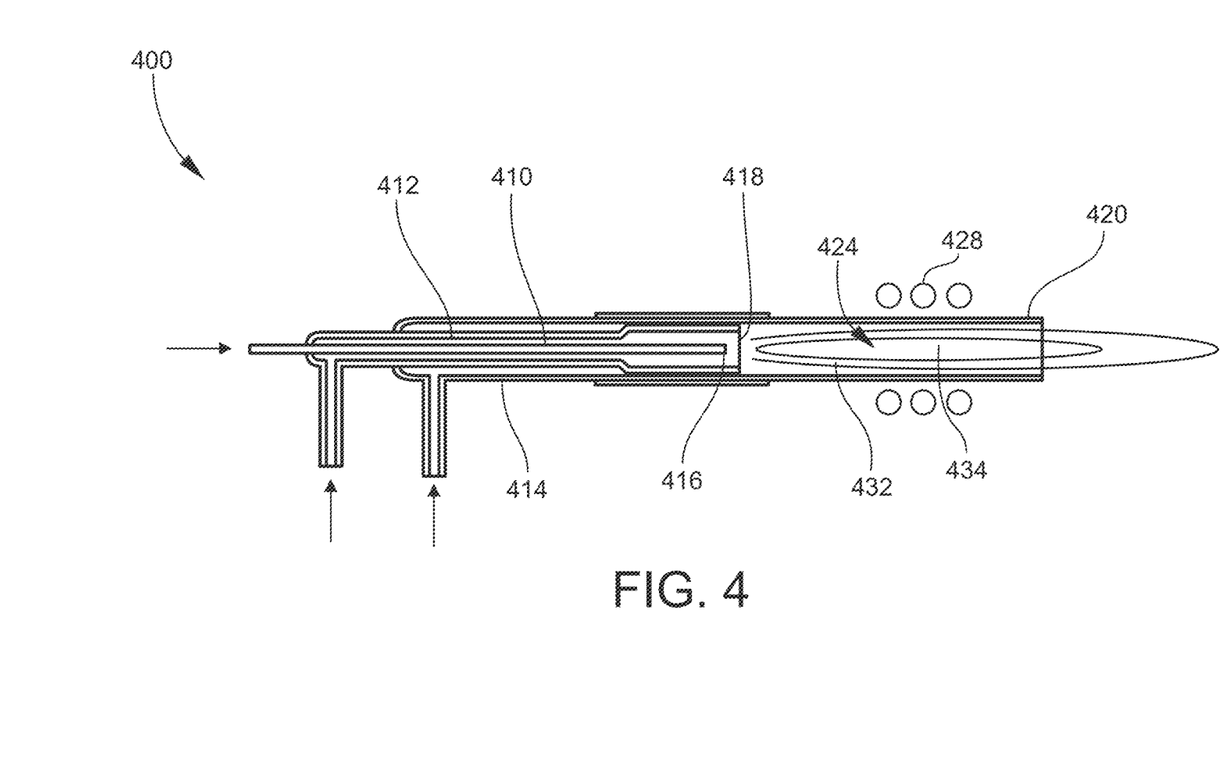
FIG. 4 is a cross-sectional view of an example of a plasma source according to some embodiments.

FIG. 4 is a cross-sectional view of an example of a plasma source 400 according to some embodiments. In this example, the plasma source 400 has a concentric tube (or plasma torch) configuration. The plasma source 400 includes a plurality of coaxial tubes that define a plurality of flow paths along the source axis. In the illustrated embodiment, a first (central) plasma source tube 410 is positioned on the source axis, a second (middle) plasma source tube 412 surrounds the first tube 410, and a third (outer) plasma source tube 414 surrounds the second tube 412. Consequently, an annular conduit or passage is formed between the first tube 410 and the second tube 412, and another annular conduit or passage is formed between the second tube 412 and the third tube 414. The axial positions of respective outlets 416, 418 and 420 of the tubes 410, 412 and 414 may be the same or different. In some embodiments, the third tube 414 is extended (or adjoins another tube) such that an interaction region 424 in which the aerosol is injected into the plasma is surrounded by the third tube 414 (or an extension thereof). The plasma source 400 also includes an energy source, which in the illustrated example includes a work coil 428 wound around the third tube 414 at the interaction region 424 for generating ICP. Alternatively, the energy source may include different components for generating other types of plasma as described above. A plasma plume 432 is shown as being discharged from the plasma source 400. In the illustrated embodiment, the second tube outlet 418 is inside the third tube 414, i.e., the second tube outlet 418 is axially upstream of the third tube outlet 420. The first tube outlet 416 may be located inside the second tube 412 for a purpose such as avoiding contact with the hot plasma. Generally, the plasma-forming gas, the sample aerosol to be interacted with the plasma, and optionally an auxiliary gas, may be fed to any of the tubes 410, 412 and 414. In some embodiments, the plasma-forming gas is supplied to the third tube 414 (and through an annular plasma-forming gas passage between the second tube 412 and the third tube 414), and the sample aerosol is supplied to the first tube 410 such that the sample aerosol is discharged into a central region 434 of the plasma plume 432, which may be a relatively cold or hollow region of the plasma. In some embodiments, the optional auxiliary gas may be supplied to the second tube 412 (and through an annular auxiliary gas passage between the first tube 410 and the second tube 412) for a purpose such as maintaining a desired flow rate from the source outlet, radially confining or controlling the shape of the plasma plume 432, and/or keeping the hot plasma away from surfaces of the plasma source 400.

In other embodiments, an auxiliary gas may not be utilized such that the intermediate second tube 412 may not be provided. In other embodiments, the plasma source 400 may not have a concentric tube configuration, and instead the sample aerosol is injected at an angle to the flow of the plasma.

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for producing an aerosol from a liquid sample, comprising:
    providing a nebulizer comprising a first nebulizer tube terminating at a first nebulizer outlet, and a second nebulizer tube coaxially surrounding the first nebulizer tube and terminating at a second nebulizer outlet;
    flowing a carrier gas through the second nebulizer tube;
    flowing the liquid sample through the first nebulizer tube such that the liquid sample becomes entrained in the carrier gas and is broken into droplets to form the aerosol; and
    flowing the aerosol out from the second nebulizer outlet, wherein:
    the liquid sample comprises a high concentration of dissolved salt or dissolved solid material; and
    the first nebulizer outlet comprises a sharp edge at which an inside diameter of the first nebulizer tube is substantially the same as an outside diameter of the first nebulizer tube, such that the sharp edge prevents accumulation of precipitates of salt or solid material at the first nebulizer outlet.

2. The method of claim 1, comprising flowing the aerosol from the second nebulizer outlet into an environment at or above atmospheric pressure.

3. A method for atomizing a liquid sample, comprising:
    producing an aerosol according to the method of claim 1;
    generating plasma; and
    injecting the aerosol into the plasma.

4. The method of claim 3, comprising flowing the aerosol at or above atmospheric pressure into an environment selected from the group consisting of:
    a plasma source in which the plasma is generated; and
    a spray chamber, followed by flowing the aerosol from the spray chamber into a plasma source in which the plasma is generated.

5. A method for analyzing a liquid sample, comprising:
    atomizing the liquid sample according to the method of claim 4 to produce sample atoms; and
    measuring an attribute of the sample atoms.

6. The method of claim 5, wherein measuring an attribute of the sample atoms is selected from the group consisting of:

measuring a spectral attribute of the sample atoms;
measuring photons emitted from the sample atoms;
directing photons emitted from the sample atoms into an optical emission spectrometer;
spectrally resolving photons emitted from the sample atoms according to wavelength, and measuring respective abundances of the wavelengths;
producing ions from the sample atoms, and measuring the ions;
producing ions from the sample atoms, and directing the ions into a mass spectrometer; and
producing ions from the atoms, spectrally resolving the ions according to mass-to-charge ratio, and measuring respective abundances of the mass-to-charge ratios.

7. A method for atomizing a liquid sample, comprising:
nebulizing the liquid sample to produce an aerosol, by flowing a carrier gas through a nebulizer, and flowing the liquid sample through the nebulizer such that the liquid sample becomes entrained in the carrier gas and is broken into droplets to form the aerosol, wherein:
   the nebulizer comprises a first nebulizer tube terminating at a first nebulizer outlet, and a second nebulizer tube coaxially surrounding the first nebulizer tube and terminating at a second nebulizer outlet;
   the liquid sample is flowed through the first nebulizer tube, the carrier gas is flowed through the second nebulizer tube, and the aerosol is emitted from the second nebulizer outlet; and
   the first nebulizer outlet comprises a sharp edge at which an inside diameter of the first nebulizer tube is substantially the same as an outside diameter of the first nebulizer tube, such that the sharp edge prevents accumulation of precipitates from the liquid sample at the first nebulizer outlet;
generating a plasma; and
injecting the aerosol into the plasma.

8. The method of claim 7, wherein the liquid sample comprises a high concentration of dissolved salt or dissolved solid material.

9. A sample atomizer, comprising:
a nebulizer comprising:
   a first nebulizer tube defining a first fluid path, and comprising an inside diameter, an outside diameter, and a first nebulizer outlet, the first nebulizer outlet comprising a sharp edge at which the inside diameter is substantially the same as the outside diameter; and
   a second nebulizer tube coaxially surrounding the first nebulizer tube and defining a second fluid path of annular cross-section, the second nebulizer tube comprising a second nebulizer outlet positioned such that the first fluid path merges into the second fluid path; and
a plasma source comprising a sample inlet communicating with the second nebulizer outlet, a plasma-forming gas inlet, and an energy source configured for generating plasma in the plasma source.

10. The sample atomizer of claim 9, wherein the first nebulizer tube comprises a tapered section along which the outside diameter is reduced down to the sharp edge.

11. The sample atomizer of claim 10, wherein the tapered section is beveled at two or more different angles relative to a central axis of the first nebulizer tube.

12. The sample atomizer of claim 9, wherein the second nebulizer outlet has a diameter substantially the same as or greater than the inside diameter of the first nebulizer tube at the first nebulizer outlet.

13. The sample atomizer of claim 9, wherein the second nebulizer outlet is free of sharp edges.

14. The sample atomizer of claim 9, wherein the second nebulizer outlet comprises a converging section or a converging-diverging section.

15. The sample atomizer of claim 9, wherein the first nebulizer tube and second nebulizer tube are coaxial with a longitudinal axis, and the second nebulizer outlet is positioned at a downstream axial distance from the first nebulizer outlet.

16. The sample atomizer of claim 9, wherein the plasma source comprises:
   a first plasma source tube communicating with the sample inlet and comprising a sample outlet;
   a second plasma source tube communicating with the plasma-forming gas inlet, the second plasma source tube coaxially surrounding the first plasma source tube and forming an annular passage; and
   an interaction region surrounded by the second plasma source tube and communicating with the sample outlet and the annular passage.

17. The sample atomizer of claim 9, wherein the plasma source comprises:
   a first plasma source tube communicating with the sample inlet and comprising a sample outlet;
   a second plasma source tube communicating with the plasma-forming gas inlet, the second plasma source tube coaxially surrounding the first plasma source tube;
   an auxiliary gas inlet;
   a third plasma source tube communicating with the auxiliary gas inlet and coaxially positioned between the first plasma source tube and the second plasma source tube, wherein an annular plasma-forming gas passage is defined between the second plasma source tube and the third plasma source tube, and an annular auxiliary gas passage is defined between the first plasma source tube and the third plasma source tube; and
   an interaction region surrounded by the second plasma source tube and communicating with the sample outlet, the annular plasma-forming gas passage, and the annular auxiliary gas passage.

18. The sample atomizer of claim 9, comprising at least one of: a liquid sample source communicating with the first nebulizer tube; a carrier gas source communicating with the second nebulizer tube; a plasma-forming gas source communicating with the plasma-forming gas inlet.

19. A sample analysis system, comprising:
the sample atomizer of claim 9; and
an analytical instrument configured to acquire data from sample atoms produced by the sample atomizer.

20. The sample analysis system of claim 19, wherein the analytical instrument is selected from the group consisting of: a spectrometer; a mass spectrometer communicating with the plasma source; and an optical emission spectrometer communicating with the plasma source.

* * * * *